US009530095B2

(12) United States Patent
Cao et al.

(10) Patent No.: US 9,530,095 B2
(45) Date of Patent: *Dec. 27, 2016

(54) METHOD AND SYSTEM FOR EXPLORING THE ASSOCIATIONS BETWEEN DRUG SIDE-EFFECTS AND THERAPEUTIC INDICATIONS

(71) Applicant: INTERNATIONAL BUSINESS MACHINES CORPORATION, Armonk, NY (US)

(72) Inventors: Nan Cao, Ossining, NY (US); Jianying Hu, Bronx, NY (US); Robert K. Sorrentino, Rye Brook, NY (US); Fei Wang, Ossining, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 324 days.

This patent is subject to a terminal disclaimer.

(21) Appl. No.: 13/970,191

(22) Filed: Aug. 19, 2013

(65) Prior Publication Data

US 2015/0006438 A1 Jan. 1, 2015

Related U.S. Application Data

(60) Provisional application No. 61/839,442, filed on Jun. 26, 2013.

(51) Int. Cl.
*G06N 5/02* (2006.01)
*G06F 19/00* (2011.01)

(52) U.S. Cl.
CPC ............ *G06N 5/02* (2013.01); *G06F 19/704* (2013.01); *G06F 19/707* (2013.01); *G06F 19/708* (2013.01)

(58) Field of Classification Search
CPC .......... G06N 5/02; G06N 5/04; G06N 99/005; G06F 19/70
(Continued)

(56) References Cited

U.S. PATENT DOCUMENTS 7,698,157 B2 4/2010 Ghouri
7,883,858 B2 2/2011 Hood et al.
(Continued)

FOREIGN PATENT DOCUMENTS

WO WO2013028480 2/2013

OTHER PUBLICATIONS

Burbidge R. et al., "Drug design by machine learning: support vector machines for pharmaceutical data analysis", Computers and Chemistry, 26, 2001, pp. 5-14.*
(Continued)

*Primary Examiner* — Stanley K Hill
*Assistant Examiner* — Dave Misir
(74) *Attorney, Agent, or Firm* — Tutunjian & Bitetto, P.C.; Louis Percello

(57) ABSTRACT

A system and method for analyzing chemical data including a processor and one or more classifiers, stored in memory and coupled to the processor, which further includes an indication predictive module configured to predict whether a given chemical treats a particular indication or not and a side effect predictive module configured to predict whether a given chemical causes a side-effect or not. A correlation engine is configured to determine one or more correlations between one or more indications and one or more side effects for the given chemical and a visualization tool is configured to analyze the one or more correlations and to output results of the analysis.

7 Claims, 5 Drawing Sheets

(58) Field of Classification Search
USPC .......................................................... 706/11
See application file for complete search history.

(56) References Cited

U.S. PATENT DOCUMENTS

| | | | |
|---|---|---|---|
| 7,979,373 | B2 | 7/2011 | Gogolak |
| 2002/0036166 | A1* | 3/2002 | Petty ....................... B01D 61/00 210/502.1 |
| 2003/0004652 | A1* | 1/2003 | Brunner ................. A01K 1/031 702/19 |
| 2006/0112105 | A1* | 5/2006 | Adamic et al. ................. 707/10 |
| 2008/0306918 | A1* | 12/2008 | Mons et al. ....................... 707/3 |
| 2010/0169853 | A1* | 7/2010 | Jain et al. .......................... 716/5 |
| 2010/0198616 | A1 | 8/2010 | Ghouri |
| 2011/0010099 | A1 | 1/2011 | Adourian et al. |
| 2011/0113002 | A1 | 5/2011 | Kane et al. |
| 2011/0262496 | A1 | 10/2011 | Desai |
| 2012/0029896 | A1* | 2/2012 | Ekins et al. .................... 703/11 |
| 2012/0265548 | A1 | 10/2012 | Hwang et al. |
| 2012/0296090 | A1* | 11/2012 | Wong et al. .................. 544/119 |
| 2012/0303388 | A1 | 11/2012 | Vishnubhatla et al. |
| 2013/0041683 | A1 | 2/2013 | Boissel |
| 2013/0138478 | A1* | 5/2013 | Hyde et al. .................. 705/7.33 |
| 2013/0144636 | A1* | 6/2013 | Pouliot et al. ..................... 705/2 |
| 2013/0179138 | A1* | 7/2013 | Jackson et al. ................. 703/11 |
| 2013/0179375 | A1* | 7/2013 | Tatonetti et al. ............... 706/12 |
| 2014/0193517 | A1* | 7/2014 | Agarwal et al. ............. 424/600 |
| 2014/0351963 | A1* | 11/2014 | Croce et al. ...................... 800/8 |

OTHER PUBLICATIONS

Kuhn M. et al., "A side effect resource to capture phenotypic effects of drugs", Molecular Systems Biology, 2010.*
Zhang P. et al., "Exploring the Relationship Between Drug Side-Effects and Therapeutic Indications", AMIA, Nov. 16, 2013, pp. 1568-1577. (Date precludes use).*
Wang F. et al., "Exploring the associations between drug side-effects and therapeutic indications", Journal of Biomedical Informatics, 51, Apr. 2014, pp. 15-23. (Date precludes use).*
Gottlieb A. et al., "PREDICT: a method for inferring novel drug indications with application to personalized medicine", Molecular Systems Biology, 2011.*
Huang L. et al., "Predicting adverse side effects of drugs", BMC Genomics, 2011, 12, (Suppl 5):S11.*
Barabasi A. et al., "Network medicine: a network-based approach to human disease", NATuRe ReVIewS, GeNetics, vol. 12, Jan. 2011.*
Hopkins A., "Network pharmacology: the next paradigm in drug discovery", Nature Chemical Biology, vol. 4, No. 11, Nov. 2008.*
Cheng F. et al., "Prediction of Drug-Target Interactions and Drug Repositioning via Network-Based Inference", PLoS Computational Biology, May 2012, vol. 8, Issue 5.*
Keiser M. et al., "Predicting new molecular targets for known drugs", Nature, vol. 462, Nov. 12, 2009.*
Zhang et al., "Computational Drug Repositioning by Ranking and Integrating Multiple Data Sources", ECML PKDD 2013, Part III, LNAI 8190, pp. 579-594, 2013.*
Kuhn et al., "The SIDER database of drugs and side effects", Nucleic Acids Research Advance Access published Oct. 19, 2015.*
Kuhn M, Letunic I, Jensen LJ, Bork P. The SIDER database of drugs and side effects. (http://www.ncbi.nlm.nih.gov/pubmed/26481350) Nucleic Acids Res. Oct. 19, 2015. doi: 10.1093/nar/gkv1075.*
Kuhn et al., "Systematic identification of proteins that elicit drug side effects", Molecular Systems Biology 9; Article No. 663; doi:10.1038/msb.2013.10, 2013.*
Campillos et al., "Drug Target Identification Using Side-Effect Similarity", Science, vol. 321, Jul. 11, 2008.*
Kuhn et al., "Large-scale prediction of drug—target relationships", FEBS Letters 582, 2008, pp. 1283-1290.*
Kuhn et al., "STITCH 3: zooming in on protein—chemical interactions", Nucleic Acids Research, 2012, vol. 40, Database issue, Published online Nov. 9, 2011.*
Wishart DS, Knox C, Guo AC, Shrivastava S, Hassanali M, Stothard P, Chang Z, Woolsey J. DrugBank: a comprehensive resource for in silico drug discovery and exploration. Nucleic Acids Res. Jan. 1, 2006;34(Database issue):D668-72. 16381955 (http://www.ncbi.nlm.nih.gov/pubmed/16381955).*
Csermely et al.; "Structure and Dynamics of Molecular Networks: A Novel Paradigm of Drug Discovery—A Comprehensive Review", Pharmacology & Therapeutic 138 (Jun. 2013),pp. 333-408.
Yang et al.; "Systematic Drug Repositioning Based on Clinical Side-Effects", PLOS ONE, www.plosone.org, vol. 6, Issue 12, E28025, Dec. 2011, pp. 1-9.
Pauwels, et al.; "Predicting Drug Side-Effect Profiles: A Chemical Fragment-Based Approach", BMC Bioinformatics, May 2011, 12:169, pp. 1-13.
Hu, et al.: "Human Disease-Drug Network based on Genomic Expression Profiles", PLOS ONE, www.plosone.org, vol. 4, Issue 8, E6536, Aug. 2009, pp. 1-11.
Campillos et al.; "Drug Target Identification Using Side-Effect Similarity", Science AAAS, vol. 321, Jul. 11, 2008, pp. 263-266.

* cited by examiner

METHOD AND SYSTEM FOR EXPLORING THE ASSOCIATIONS BETWEEN DRUG SIDE-EFFECTS AND THERAPEUTIC INDICATIONS

RELATED APPLICATION INFORMATION

This application claims priority to provisional application Ser. No. 61/839,442 filed on Jun. 26, 2013, incorporated herein by reference in its entirety.

BACKGROUND

Technical Field

The present invention relates to prediction tools, and more particularly to predicting the associations between drug side-effects and therapeutic indications.

Description of the Related Art

Inferring potential therapeutic indications (e.g., drug repositioning), for either novel or approved drugs, has become a key approach in drug development. Recently, a number of computational methods have been developed to predict drug indications. There are four typical computational strategies in drug repositioning: (1) predicting drug indications on the basis of the chemical structure of the drug; (2) inferring drug indications from protein targets interaction networks; (3) identifying relationships between drugs based on the similarity of their phenotypic profiles; and (4) integrating multiple properties (e.g., chemical, biological, or phenotypic information) of drugs and diseases to predict drug indications.

These strategies focus primarily on using preclinical information using either chemical structures or protein targets, but clinical therapeutic effects are not always consistent with preclinical outcomes. Such chemical and biological information exhibits translational issues and is noisy when off-target binding occurs. Existing studies have build disease-side-effect associations based on all known drug-disease and drug-side-effect information, but such associations are very limited in number, and are biased from current observations.

SUMMARY

A system for analyzing chemical data comprising a processor; one or more classifiers, stored in memory and coupled to the processor, further comprising an indication predictive module configured to predict whether a given chemical treats a particular indication or not and a side effect predictive module configured to predict whether a given chemical causes a side-effect or not; a correlation engine configured to determine one or more correlations between one or more indications and one or more side effects for the given chemical; and a visualization tool configured to analyze the one or more correlations and to output results of the analysis.

A method for analyzing chemical data, comprising classifying, using one or more classifiers stored in memory and coupled to a processor, wherein classifying further comprises predicting whether a given chemical treats one or more indications or not using an indication prediction module and predicting whether a given chemical causes one or more side effects or not using a side-effect predictive module; determining one or more correlations between one or more indications and one or more side effects for the given chemical using a correlation engine module; and analyzing the one or more correlations and outputting results using a visualization tool.

A computer readable storage medium comprising a computer readable program, wherein the computer readable program when executed on a computer causes the computer to perform the steps of classifying, using one or more classifiers stored in memory and coupled to a processor, wherein classifying further comprises predicting whether a given chemical treats one or more indications or not using an indication prediction module and predicting whether a given chemical causes one or more side effects or not using a side-effect predictive module; determining one or more correlations between one or more indications and one or more side effects for the given chemical using a correlation engine module; and analyzing the one or more correlations and outputting results using a visualization tool.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
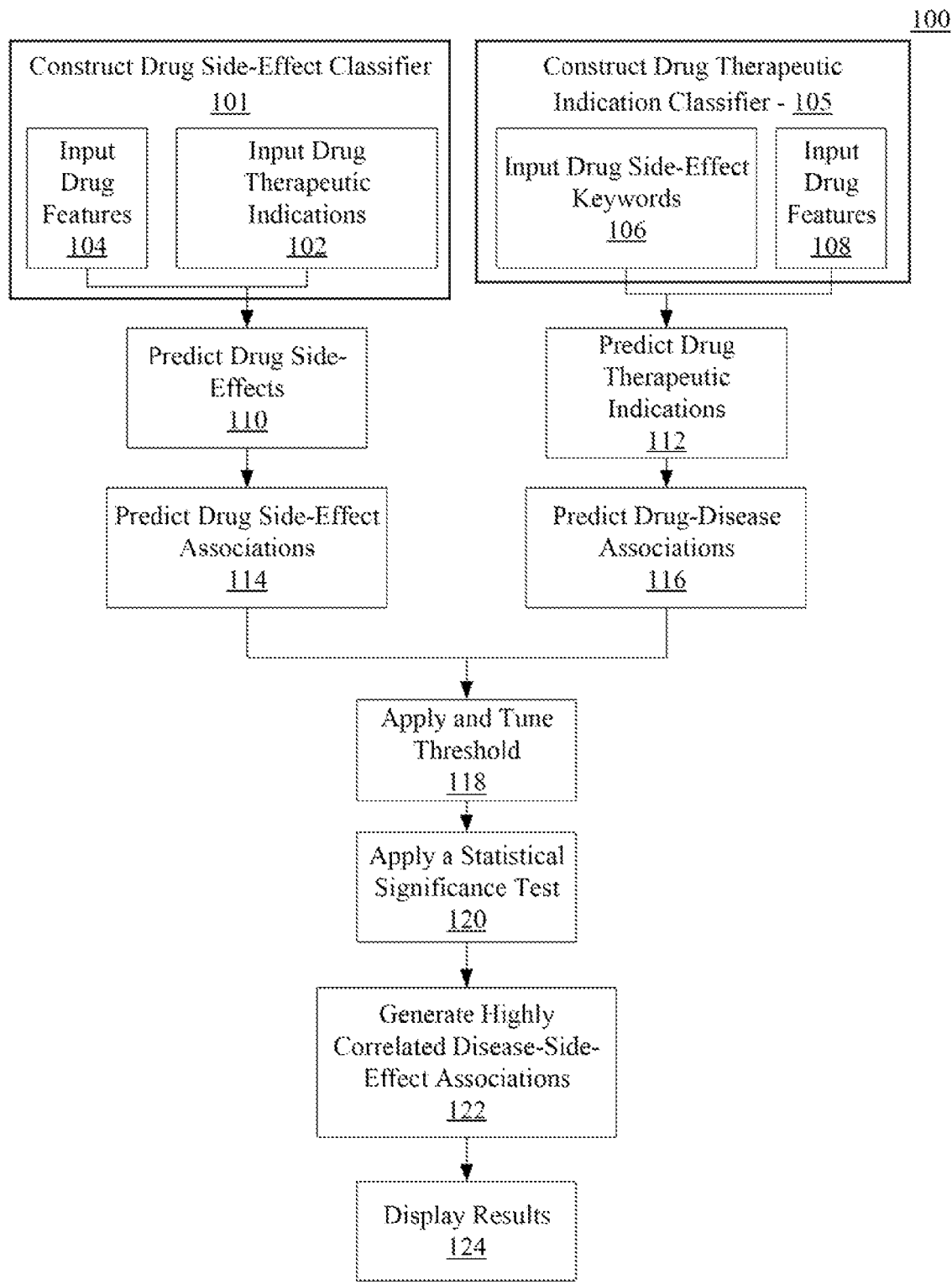
FIG. 1 is block/flow diagram showing a method for correlating and predicting drug side-effects and therapeutic indications in accordance with the present principles.

A methodology for predicting the associations between drug side-effects and therapeutic indications is provided according to the present principles. A visualization tool may also be provided for exploring the associations between the predicted drug side-effects and therapeutic indications. A method for predicting the relationships between drug side-effects and therapeutic indications may include constructing a drug therapeutic indication classifier for predicting whether a given drug treats a particular disease or not, and this process may be repeated for all diseases. Features that may be employed for building the classifier include a drug's clinical side-effect keywords and other drug properties (e.g., chemical structures, protein targets).

A drug side-effect classifier may be constructed for predicting whether a given drug causes a side-effect or not, and this process may be repeated for all side-effects. Features that may be employed for building the classifier may include a drug's known uses (e.g., therapeutic indications) and other drug properties (e.g., chemical structures, protein targets, etc.). Highly correlated disease-side-effect associations may be constructed from the predicted drug-disease and drug-side-effect associations by using a statistical significance test (e.g., Fisher's exact test).

The visualization system for analyzing the predicted associations between drug side-effects and therapeutic indications may include one or more of a network-based representation for disease-side-effect associations, an adjustable tuning bar that can tune the threshold of the association strength (measured by p-value, probability, etc.), a user interface (UI), which may display the associations, a dynamic layout strategy that can show the bi-cliques formed by those predicted associations while tuning the association strength, and a zoom-in/zoom-out functionality that allows the user to investigate the detected associations at different granularities. Thus, the present invention may relate diseases to side-effects (and vice versa), even in cases where the precise pharmacological mechanism is unknown.

Determining strongly correlated disease-side-effect pairs is beneficial for drug discovery. For example, the side-effect information may be employed to repurpose existing treatments. Furthermore, if a new treatment is designed for a specific disease, health care stakeholders (e.g., regulators, providers, patients and pharmaceutical companies) may employ the present principles to discover adverse reactions in the highly correlated side-effect list of the disease, and may control the formulation and dosing of drugs in the clinical trials to prevent serious safety issues.

Therapeutic indications (e.g., drug's indicated diseases) and side-effects are both measureable behavioral or physiological changes in response to the treatment. Intuitively, if drugs treating a disease share the same side-effects, this may be manifestation of some underlying mechanism-of-action (MOA) linking the indicated disease and the side-effect. In other words, the phenotypic expression of a side-effect can be correlated to that of a disease. This provides the basis to relate diseases to side-effects (and vice versa), even in cases where the precise pharmacological mechanism is unknown. Furthermore, both therapeutic indications and side-effects are observations on human in the clinical stage, so there is less of a translational issue. Therapeutic indications may be employed to predict side effects, and side-effects may be employed to predict therapeutic indications, as they may each be an effective predictive factor of the other.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a block/flow diagram illustratively depicting a method for correlating and predicting drug side-effects and therapeutic indications 100 in accordance with the present principles is shown. In one embodiment, a drug side-effect classifier 101 may be constructed for predicting whether a given drug treats a particular disease or not, and this process may be repeated for all diseases. The data that is input when building the classifier may be drug therapeutic indications 102 (e.g., drug's known uses) and other drug properties 104 (e.g., chemical composition, biological features, protein targets, etc.). Predicted drug side-effects may be obtained in block 110, and predicted drug side effect associations may be obtained in block 114 using the drug side-effect classifier 101.

In one embodiment, a therapeutic indication classifier 105 may be constructed for predicting whether a given drug causes a particular side-effect or not, and this process may be repeated for all side-effects. The data that is input when building the classifier may be a drug's clinical side-effect keywords 106 and other drug properties 108 (e.g., (e.g., chemical composition, biological features, target proteins, etc.). Predicted drug therapeutic indications may be obtained in block 112, and predicted drug-disease associations may be obtained in block 116 using the drug therapeutic indication classifier 105.

In one embodiment, a threshold of correlation may be selected, applied, and tuned in block 118, and highly correlated disease-side-effect associations may be generated in block 122 from the predicted drug-disease and drug-side-effect associations by applying a statistical significance test in block 120 (e.g., Fisher's exact test). The results may be displayed in block 124 on a display device.

Figure 2:
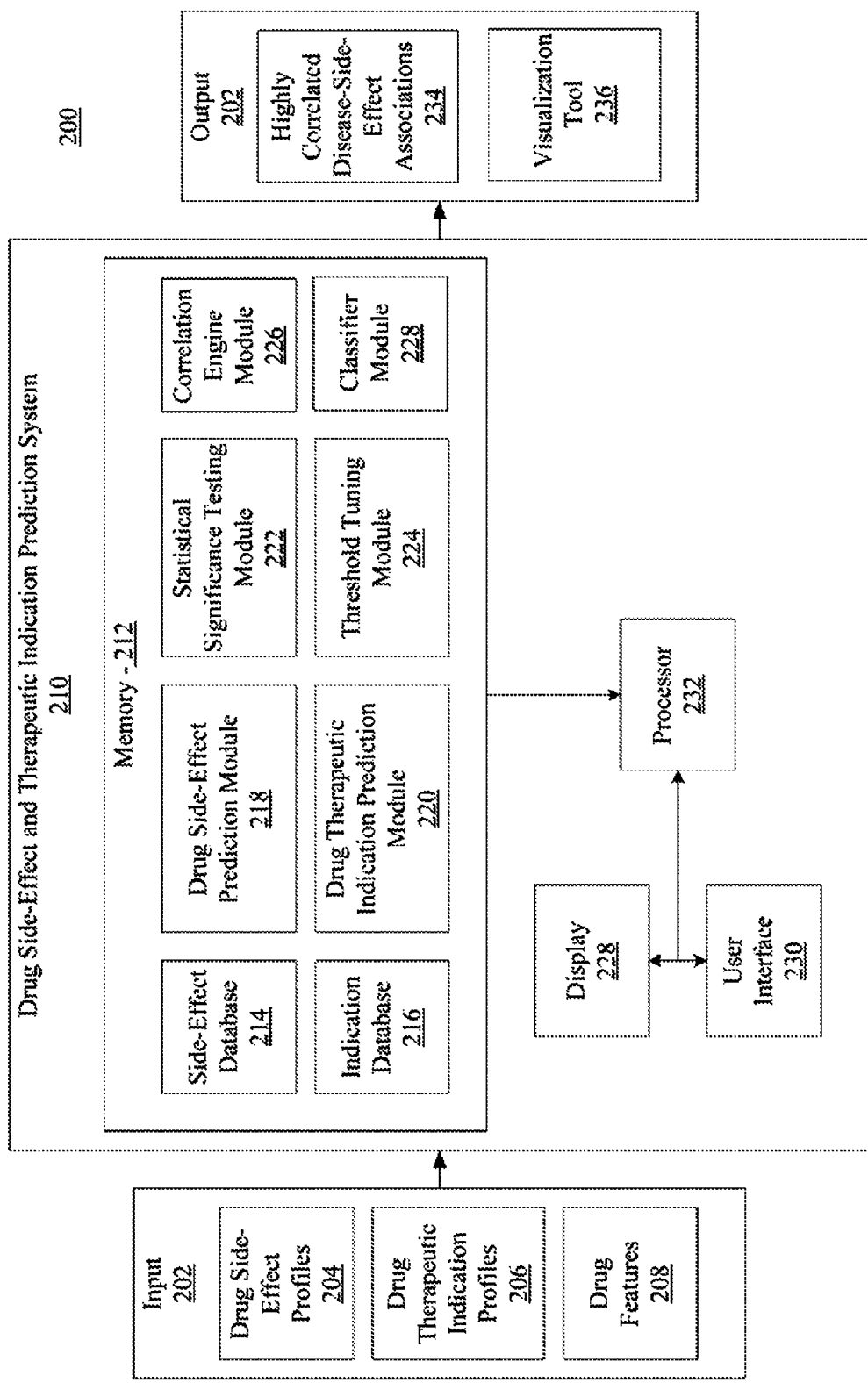
FIG. 2 is block/flow diagram showing a system for correlating and predicting drug side-effects and therapeutic indications in accordance with the present principles.

Referring to FIG. 2, a computer system for correlating and predicting drug side-effects and therapeutic indications 200 is illustratively shown according to one embodiment of the present principles. In one embodiment, the input 202 to the system may be drug side-effect profiles 204, drug therapeutic indication profiles 206, and/or drug features 208, and the system may include a processor 232. The system not only may employ all known drug-disease and drug-side-effect information but also may employ the predicted highly correlated drug-disease and drug-side-effect information in block 234.

In one embodiment, a computer system may include an indication database 216 which may have one or more indications for each of one or more drugs (e.g., chemicals), the indications being a description of the purpose of use for the drug. The system may include a side-effect database 214 having one or more side-effects for each of one or more drugs, the side effects being effects of use of the drug or chemical that are outside of the purpose of use of the drug or chemical. A drug side effect prediction module 218 may be employed to predict unknown side-effects for drugs, and a drug therapeutic indication prediction module 220 may be employed to predict unknown therapeutic indications for drugs. A statistical significance testing module 222 may be employed to determine hidden correlations between drug side-effects and therapeutic indications using, for example, Fisher's exact test, which is an approach for measuring the significance of the association between two nominal variables (e.g., each side-effect vs. each disease). In one embodiment, a threshold may be tuned in block 224, disease-side-effect profiles (the most likely side-effects by the drugs which treat a specific disease) may be built based on known drug-disease and drug-side-effect relationships.

In one embodiment, the approved drugs from DrugBank, which is a public database of drug information, may be employed as input 202. From DrugBank, a plurality of approved small-molecule drugs (e.g., 1447) may be collected. These drugs may be mapped to other drug resources (e.g., PubChem®, Unified Medical Language System (UMLS®)) to extract other drug related information. For example, chemical structures of a plurality of drugs (e.g., 1103) may be extracted from PubChem®, and to encode the drug chemical structure, a fingerprint corresponding to 881 chemical substructures defined in the PubChem® may be employed. Each drug may be represented by an 881-dimensional binary profile whose elements encode for the presence or absence of each PubChem® substructure by 1 or 0, respectively. In this example, there may be 132,092 associations between drugs and chemical substructures in the dataset, and each drug may have 119.8 substructures on average.

In one embodiment, target information of each drug may be extracted from an indication database 216, such as, for example, the DrugBank. To facilitate collecting target protein information, target proteins may be mapped to a knowledgebase such as, for example, the UniProt™ Knowledgebase, which is a central knowledgebase including comprehensive and complete information on proteins. In one embodiment, 3,152 relationships between 1,007 drugs and 775 proteins may be extracted, and each drug may have 3.1 protein targets on average. Each drug may be represented by a 775-dimensional binary profile whose elements may encode for the presence or absence of each target protein by 1 or 0, respectively.

In one embodiment, side-effect keywords may be obtained from a side effect database 214, such as, for example, the Side Effect Resource (SIDER) database, which contains information about marketed medicines and their recorded adverse drug reactions. From the SIDER database, a dataset containing 888 small-molecule drugs and 1385 side-effect keywords may be constructed. Each drug may be represented by a 1385-dimensional binary profile whose elements encode for the presence or absence of each of the side-effect keywords by 1 or 0, respectively. In one embodiment, the statistics of side-effect data are then obtained.

For example, in one embodiment according to the present principles, 69% of drugs may have between 10 and 100 different side effects; 22% of drugs may have more than 100 side-effects; and 9% of drugs may have less than 10 side-effects. Also, in one embodiment, 56% of all side-effects may occur for <10 drugs; 32% of all side-effects may occur for 10-100 drugs; and 12% of all side-effects may occur for >100 drugs. Altogether, 61,102 associations between drugs and side-effect terms in the dataset may be obtained, and each drug may have 68.8 side-effects on average.

In one embodiment according to the present principles, known drug uses may be obtained through extracting treatment relationships between drugs and diseases from the National Drug File-Reference Terminology (NDF-RT®). After normalizing various drug names in NDF-RT® to their active ingredients, therapeutic indications may be extracted for 799 drugs out of the 1103 drugs (discussed above), which may construct 3250 treatment relationships between 799 drugs and 719 diseases. Thus each drug may be represented by a 719-dimensional binary profile whose elements encode for the presence or absence of each of the therapeutic indications by 1 or 0, respectively. In one embodiment, the statistics of therapeutic indications data is as follows. Most of drugs (75%) may treat <5 indicated disease; 18% of drugs may treat 5 to 10 diseases; and 7% of drugs may treat >10 diseases. For example, although the disease Hypertension may have 78 related drugs, 80% of diseases may have only <5 drugs; 10% of diseases may have 5-10 drugs; and the remaining 10% of diseases may have >10 drugs.

In one embodiment, drug indication prediction tasks and drug side-effect prediction tasks may be modeled as binary classification problems. For example, for indication prediction, a classifier module 228 may be employed for constructing a classifier to predict whether a given drug treats a particular disease or not, and this process may be repeated for all diseases. For side-effect prediction, a classifier module may be employed for constructing a classifier for predicting whether a given drug x has a side-effect or not, this process may be repeated for all side-effects.

In one embodiment, a statistical significance testing module 222 may be employed using, for example, Fisher's exact test, and a threshold may be adjusted using a threshold tuning module 224. A correlation engine module 226 may be employed for each of one or more of the drugs/chemicals determines a correlation (e.g., of occurrence) between one or more of the drug indications and one or more of the drug side effects. In one embodiment, the output 202 may be highly correlated disease-side-effect associations 234, and the correlation may be analyzed and the results may be output using a visualization tool 236.

The system may include a clustering engine within the correlation engine module 226 that clusters the indications and side effects (the correlation may be done for each drug or may be independent of the drug) within a selected threshold of correlation. The correlations may be done for each drug. The selected threshold of correlation may be variable. One or more graphical user interfaces (GUI) 230 may display on a display device 228 one or more of the clusters of indications and side effects where the proximity (edges of the cluster) of the indications and side effects is determined by (e.g., is proportional to) the respective correlation. The positions of the cluster may remain substantially the same on the GUI 230 irrespective of the selected threshold of correlation.

In one embodiment, the indications may be received from one or more of the following sources: clinical studies, trials, drug development, empirical information, etc. The side effects may be received from one or more sources, including, for example, clinical studies, trials, drug development, empirical information, etc. The side effects may be received from one or more of the following sources: clinical studies, trials, drug development, empirical information, FDA drug label, FDA Adverse Event Reporting System (FAERS), real-world evidence, etc.

Figure 3:
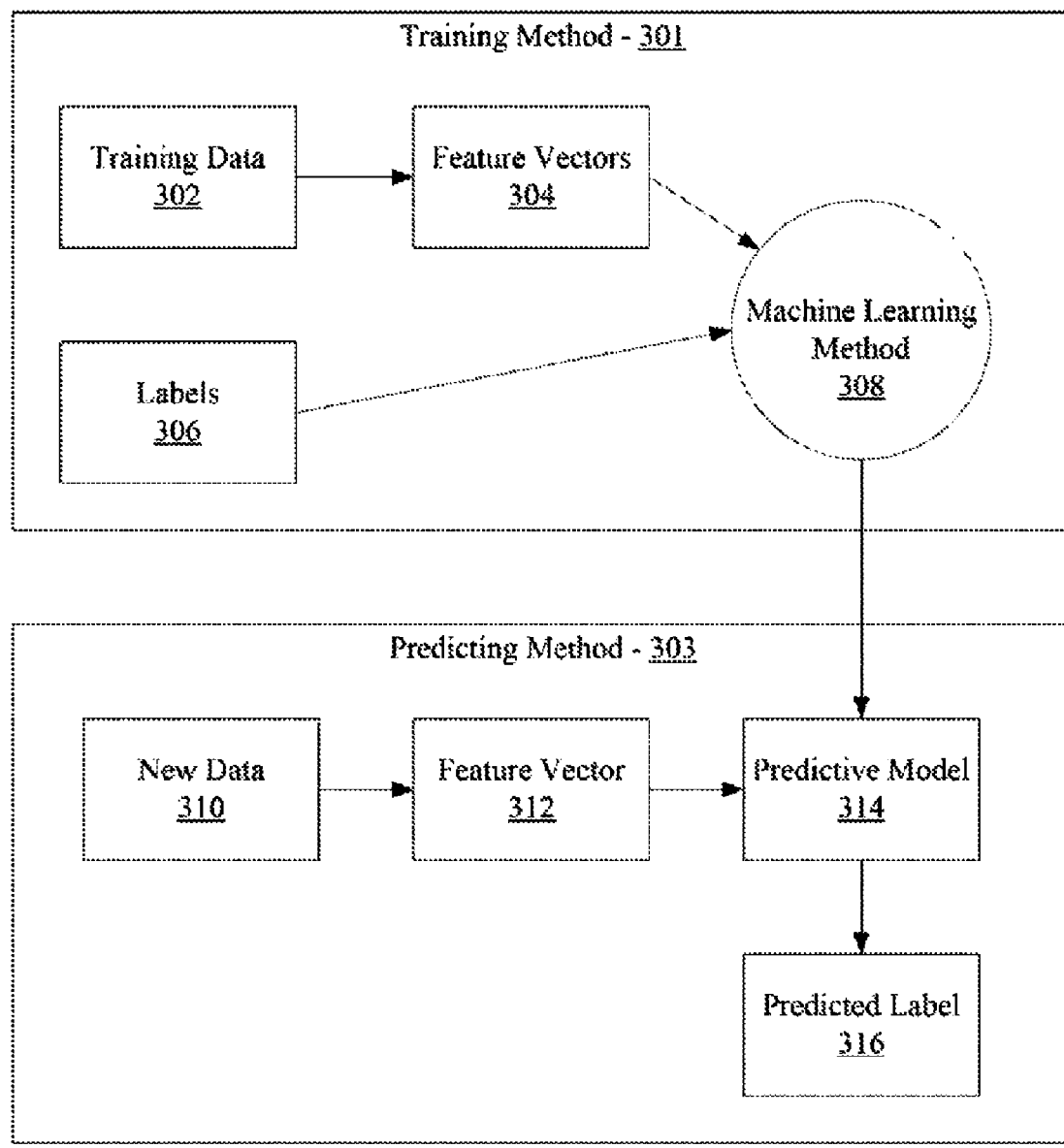
FIG. 3 is block/flow diagram showing a method for predicting therapeutic indications and side effects based on a supervised learning framework in accordance with the present principles.

Referring now to FIG. 3, a method for predicting therapeutic indications and side effects based on a supervised learning framework 300 in accordance with the present principles is illustratively depicted. In one embodiment, the training method is depicted in block 301 and the predicting method is depicted in block 303.

In one embodiment, both therapeutic indication prediction and side-effect prediction tasks are based on the standard supervised learning framework. For example, with therapeutic indication prediction, the examples with labels may be a training dataset 302 (e.g., the drugs with known indications). A label is provided in block 306 (e.g., Label $y \in \{0,1\}$, where 0 means the drug cannot treat the indicated disease and 1 means the drug does treat the indicated disease). Because we have the chemical, biological, and phenotypic information for drugs, we can represented them as high-dimensional (e.g., 881+775+1385 features) feature vectors 304 x). A machine learning method may be applied in block 308, and supervised learning methods may determine a function $f$ to obtain the result of $y=f(x)$.

In one embodiment, new data 310 (e.g., the drugs we don't know indications), may be introduced, and the $f$ may be applied to its feature vector 312 to obtain a predictive model 314 along with a predicted label 316. This method may be repeated for all possible diseases to obtain the relationships between all drugs and all diseases. Similarly, the side-effect prediction may be obtained by using a similar method.

Figure 4:
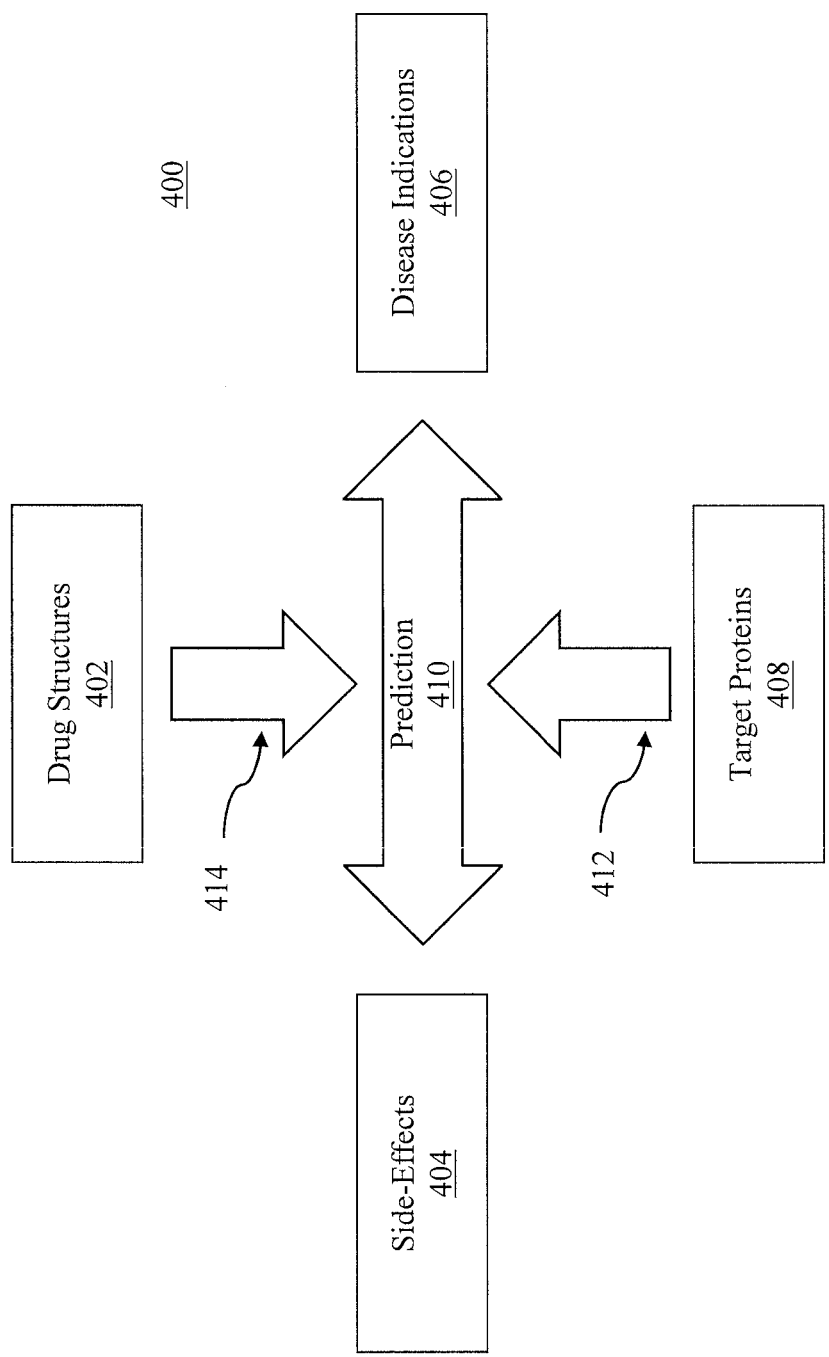
FIG. 4 is a block/flow diagram showing a high level overview of the data which may be employed to correlate and predict drug side-effects and therapeutic indications in accordance with the present principles.

Referring to FIG. 4, a block/flow diagram illustratively depicting a high level overview of the data which may be employed to correlate and predict drug side-effects and therapeutic indications 400 in accordance with the present principles. In one embodiment, Drug structures 402 may be integrated with side effects and disease indications in block 414 and target proteins 408 may be integrated with side effects and disease indications in block 412 to obtain predictions of side-effect and disease indication associations. Side effects may be, for example, weight loss, impotence, dizziness, blurred vision, etc., while disease-indications may be hypertension, diabetes, asthma, pain, etc.

For example, in one embodiment, for therapeutic indication prediction, the following sources may be employed in accordance with the present principles: (1) chemical (881 substructure features); (2) biological (775 protein target features); (3) side-effect (1385 side-effect keywords); (4) chemical+biological (881+775 features); (5) chemical+side-effect (881+1385 features); (6) biological+side-effect (775+1385 features); (7) chemical+biological+side-effect (881+775+1385 features). It is noted that the above-mentioned sources are for illustration purposes only, and it is contemplated that other sources may also be employed in accordance with the present principles.

For example, in one embodiment, for side-effect prediction task, the following sources may be employed in accordance with the present principles: (1) chemical (881 substructure features); (2) biological (775 protein target features); (3) indication (719 disease-indication features); (4) chemical+biological (881+775 features); (5) chemical+indication (881+719 features); (6) biological+indication (775+719 features); (7) chemical+biological+indication (881+775+719 features). It is noted that the above-mentioned sources are for illustration purposes only, and it is contemplated that other sources may also be employed in accordance with the present principles.

Figure 5A:
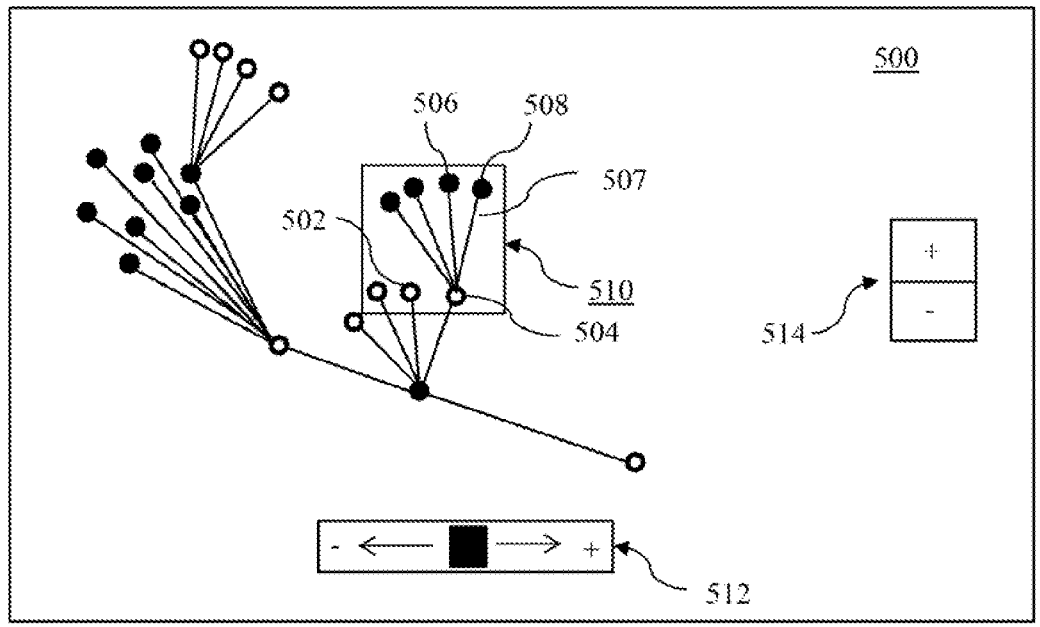
FIG. 5A is an illustrative depiction of a visualization tool/graph which shows disease-side-effect associations in accordance with the present principles.

Referring to FIG. 5A, a visualization tool which may analyze and/or output disease-side-effect associations 500 is illustratively shown in accordance with the present principles. In one embodiment, the visualization system 500 (e.g., on-line tool) may analyze the predicted associations between drug side-effects and therapeutic indications may have following features: A network-based representation for disease-side-effect associations may be provided. An adjustable tuning bar 512 may be provided that may tune the threshold of the association strength, which may be measured by p-value, probability, above which the associations will be showed in a user interface (UI) (not shown). A dynamic lay-out strategy can show the bi-cliques formed by those predicted associations while tuning the association strength. Bi-cliques may be shown for selected areas of the visualization tool/graph 510, where particular points (e.g., solid circles) 506 and 508 of the graph may represent different diseases, and other points 502 and 504 (e.g., outline circles) of the graph may represent different side-effects, while association strengths may be depicted as edges 507. A zoom-in/zoom-out functionality 514 may allow the user to investigate the detected associations at different granularities. The visualization tool may also be configured to output the analyzed results in any suitable medium. It is noted that while this particular area of the visualization tool/graph is illustratively depicted according to the present principles, larger tools/graphs and other sorts of tools/graphs are also contemplated according to the present principles.

In one embodiment, a visualization of a disease-side-effect association tree is shown making connections between drugs or chemical and their side effects in accordance with one embodiment. It is noted that the present invention is not limited to drug analysis, as it may be employed for any chemical that has a purpose and a side effect. For example, the chemicals employed to clean up an oil spill dispersed the oil, but may have had some side effect on the ecosystem. The present principles may be extended to any type of chemical and any type of side-effects in different domains. For example, a dynamic layout strategy that can show bi-cliques formed by predicted associations between drugs, side-effects and diseases 502, 504, 506, 508 (points) and their association strength 507 (edges) may be employed according to the present principles.

Figure 5B:
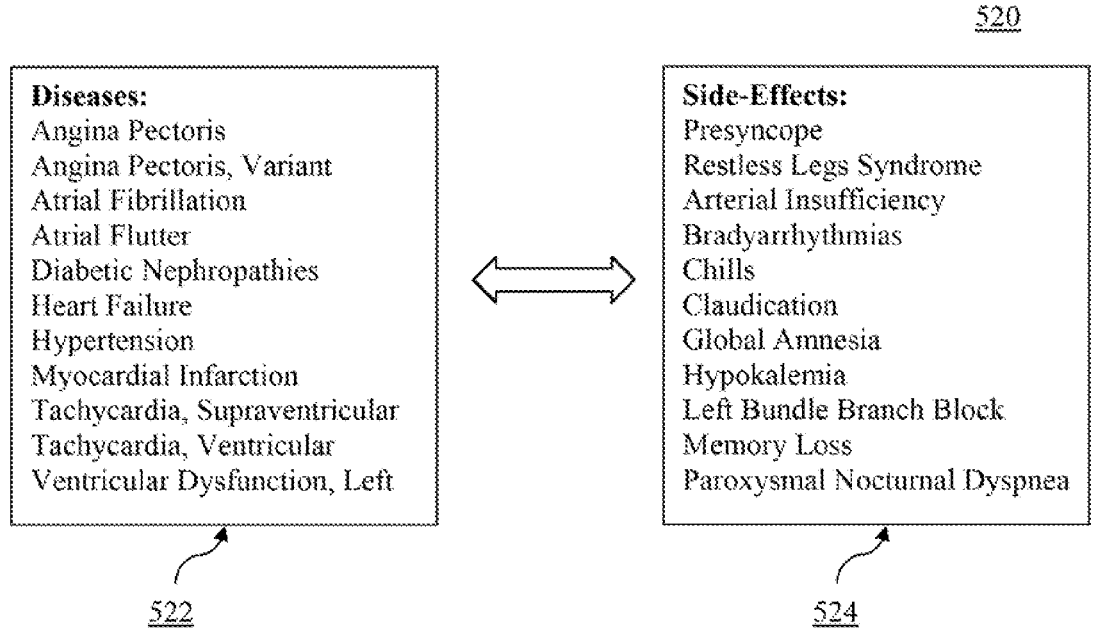
FIG. 5B is a block/flow diagram showing an example of a portion of a bi-clique disease-side-effect graph in accordance with the present principles.

Referring now to FIG. 5B, a block/flow diagram depicting a bi-clique example of a portion of a disease-side-effect graph 520 is illustratively shown in accordance with the present principles. In one embodiment, a list of diseases obtained from the visualization tool may be displayed in block 522, while a list of side effects obtained from the visualization tool may be displayed in block 524. It is noted that while this particular portion of the visualization tool/graph is illustratively depicted in a bi-clique graph according to the present principles, other portions of a visualization tool, and other sorts of graphs are also contemplated according to the present principles.

Having described preferred embodiments of a method and system for exploring the associations between drug side-effects and therapeutic indications (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for analyzing chemical data, comprising:
classifying, using one or more classifiers stored in memory and coupled to a processor, wherein classifying further comprises:
constructing a dataset from a plurality of side-effect database sources, the dataset including a plurality of clinical side-effect keywords for a plurality of chemicals;
predicting whether a given chemical treats one or more indications or not based on a combination on the clinical side-effect keywords and other chemical properties of the given chemical using an indication prediction module; and
predicting whether the given chemical causes one or more side effects or not using a side-effect predictive module;
determining one or more correlations between one or more indications and one or more side effects for the given chemical using a correlation engine module; and
analyzing the one or more correlations and outputting results using a visualization tool.

2. The method as recited in claim 1, wherein features used for predicting whether the given chemical causes the one or more side-effects include the chemical's known uses and other chemical properties of the given chemical.

3. The method as recited in claim 1, further comprising applying a statistical significance test to build correlated disease-side-effect associations from predicted chemical-disease and chemical-side-effect associations.

4. The method as recited in claim 1, further comprising clustering the predicted indications and side effects for the chemical within a selected threshold of correlation using a clustering engine, wherein the selected threshold of correlation is variable.

5. The method as recited in claim 1, further comprising tuning a threshold of association strength above which at least one of drug-disease or drug-side-effect associations will be shown in the visualization tool, and investigating the associations at different granularities using a zoom-in/zoom-out function.

6. The method as recited in claim 5, further comprising representing disease-side-effect associations configured to show bi-cliques formed by the associations while tuning the threshold of association strength using a network-based dynamic layout strategy.

7. The method as recited in claim 1, wherein the predicting of the indications and the side effects includes predictions related to one or more chemicals interacting with one or more environmental ecosystems.

* * * * *